United States Patent [19]
Bekki et al.

[11] Patent Number: 5,007,932
[45] Date of Patent: Apr. 16, 1991

[54] ARTIFICIAL BONE JOINT

[75] Inventors: Katsutoshi Bekki; Kazuo Kondo; Yoshimasa Shibata; Shigeo Niwa, all of Aichi, Japan

[73] Assignee: NGK Spark Plug Co., Ltd., Aichi, Japan

[21] Appl. No.: 316,526

[22] Filed: Feb. 27, 1989

Related U.S. Application Data

[63] Continuation of Ser. No. 865,825, May 22, 1986, abandoned, which is a continuation-in-part of Ser. No. 817,116, Jan. 8, 1986, abandoned.

[30] Foreign Application Priority Data

Jan. 8, 1985 [JP] Japan .................. 60-738[U]
Jan. 8, 1985 [JP] Japan .................. 60-739[U]
Jan. 8, 1985 [JP] Japan .................. 60-776[U]

[51] Int. Cl.⁵ .......................... A61F 2/30; A61F 2/42
[52] U.S. Cl. .......................... 623/18; 623/21
[58] Field of Search ................. 623/16, 18, 19, 20, 623/21, 22, 23

[56] References Cited

U.S. PATENT DOCUMENTS

| | | | |
|---|---|---|---|
| 3,805,302 | 4/1974 | Mathys | 623/21 |
| 3,816,854 | 6/1974 | Schlein | 623/18 |
| 3,889,300 | 6/1975 | Smith | 623/18 |
| 3,924,277 | 12/1975 | Freeman et al. | 623/18 |
| 3,946,445 | 3/1976 | Bentley et al. | 623/18 |
| 3,991,425 | 11/1976 | Martin et al. | 623/18 |
| 4,031,571 | 6/1977 | Heimke et al. | 623/23 |
| 4,040,130 | 8/1977 | Laure | 623/21 |
| 4,064,568 | 12/1977 | Grundei et al. | 623/18 |
| 4,184,213 | 1/1980 | Heimke | 623/18 |
| 4,231,121 | 11/1980 | Lewis | 623/18 |
| 4,242,759 | 1/1981 | White | 623/21 |
| 4,272,855 | 6/1981 | Frey | 623/16 |
| 4,281,419 | 8/1981 | Treace | 623/10 |
| 4,298,992 | 11/1981 | Burstein et al. | 623/20 |
| 4,304,011 | 12/1981 | Whelan | 623/21 |
| 4,501,031 | 2/1985 | McDaniels et al. | 623/20 |
| 4,516,569 | 5/1985 | Evans et al. | 623/18 |
| 4,634,444 | 1/1987 | Noiles | 623/20 |
| 4,685,919 | 8/1987 | Niwa et al. | 623/21 |

FOREIGN PATENT DOCUMENTS

| | | | |
|---|---|---|---|
| 493526 | 5/1950 | Belgium | 623/23 |
| 3528204 | 2/1986 | Fed. Rep. of Germany | 623/20 |
| 2269324 | 1/1976 | France | 623/18 |
| 50-28197 | 3/1975 | Japan . | |
| 52-30096 | 3/1977 | Japan . | |
| 54-127197 | 10/1979 | Japan . | |
| 56-130148 | 10/1981 | Japan . | |
| 0990214 | 1/1983 | U.S.S.R. | 623/20 |
| 1304837 | 1/1973 | United Kingdom | 623/18 |
| 2119655 | 11/1983 | United Kingdom | 623/16 |

Primary Examiner—David J. Isabella
Attorney, Agent, or Firm—Finnegan, Henderson, Farabow, Garrett and Dunner

[57] ABSTRACT

An artificial joint has a first member mounted on a first bone and a second member mounted on a second member. An angle defined between the first and second members is variable. The first member has a convex curved surface and the second member has a concave curved surface with is in sliding contact with the convex curved surface. A groove is formed in one of the first and second members and a boss inserted into the groove for limiting the sliding movement of the joint in a single plane is formed in the other of the members. Also, an artificial fixed knuckle bone is disclosed.

23 Claims, 7 Drawing Sheets

ARTIFICIAL BONE JOINT

This application is a continuation of application Serial No. 06/865,825, filed May 22, 1986 now abandoned which in turn is a continuation-in-part of application Ser. No. 06/817,116 filed Jan. 8, 1986, now abandoned

BACKGROUND OF THE INVENTION

This invention relates to an artificial joint and more particularly to anchors of the artificial joint, the anchors being inserted into a bone.

There have been proposed and used various structures of joint portions for artificial articulations, wherein a spherical joint end is used in combination with an associated concave joint end; joint ends having through holes are coupled by a pin; and an elastic material is used for the joint portion.

In the structure in which a spherical joint end is used together with a concave joint end, a high accuracy in configuration is needed for smooth movement. Also, a manufacturing process thereof is time-consuming and needs a great amount of labor. One of the joint ends is rotated in a universal direction relative to the other so that it is impossible to apply such joint structure to an articulation where two components should be rotated in a single plane as in a finger joint.

In the structure of pin-joint, the number of necessary components such as pins is increased and in assembling work for embedding the joint structure in the patient's articulation needs a long period of time. In addition, a large load is applied to the thin pin, resulting in reduction in durability and wear resistance.

In the elastic structure of joint, the movement of the joint is limited and it is necessary to keep the joint in a folded state with a continuous force.

On the other hand, there has been used an artificial joint having two anchors each inserted into a bone, the anchors being coupled having an angle changeable to each other. The anchors may be cylindrical, square or bar-shaped and generally have smooth surfaces (Japanese Pat. Appln. Laid-Open Nos. 54-127197, 52-30096, 50-18197). The smooth surface allows the anchor inserted to move in the direction of insertion or opposite thereto and connection with the bone is slow. Consequently, the bone must be screwed laterally and this requires time and labor for such an operation.

Figure 9:
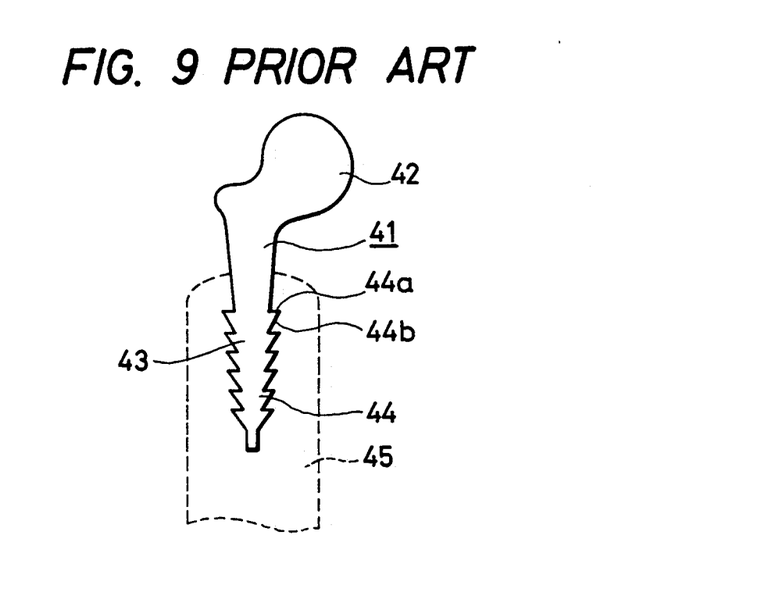
FIG. 9 is a schematic view of a conventional artificial joint.

There has also been proposed an anchor having a boss on the surface to solve the above problem (Japanese Pat. Appln. Laid-Open No. 56-130148). In FIG. 9, there is shown an artificial joint comprising an inner male member 41 having two parts, a first curved portion 42 for engaging with a female part and a second anchor portion 43 having bosses 44 consisting of faces 44a directed to the curved portion 42 and faces 44b directed opposite thereto. The face 44a is substantially perpendicular to the axis of the anchor 43, thus ensuring that the anchor 43 is hard to draw out of a bone 45.

An artificial joint of the above-described sort cannot be fixed until the tissue of the bone 45 is completely coupled to the surface of the anchor 43. However, a long period of time is needed for the bone to completely couple to the anchor portion 43, similarly to a member whose anchor has a smooth surface

SUMMARY OF THE INVENTION

It is therefore an object of the present invention to provide an artificial joint that can quickly be coupled to the bone fixed by facilitating the growth and fixture of bone tissue.

In order to solve the above-described problems, the following structure has been adopted.

According to the present invention, in an artificial joint having a first member mounted on a first bone and a second member mounted on a second bone, there has been provided an angle defined between said first member and said second member that is variable. The artificial joint is characterized in that said first member has a convex curved surface and said second member has a concave curved surface which is in sliding contact with said convex curved surface. A groove is formed in one of said first and second members and a boss, inserted into the groove for limiting the sliding direction of the joint, is formed in the other of said first and second members.

There has also been provided an anchor structure of an artificial joint having two anchors, one anchor inserted in one bone and the other anchor inserted in another bone, and curves for adjusting angles of the two anchors characterized in that recesses or bosses are formed on the surface of the anchor and a face having the recesses or bosses and facing the direction of insertion of the anchor form an angle of less than 100 degrees to the direction of insertion.

BRIEF DESCRIPTION OF THE DRAWINGS

FIGS. 1A to 1C are the schematic views of an embodiment of the present invention.

FIGS. 2A to 2G illustrate a first member embodying the present invention.

FIGS. 3A to 3G illustrate a second member according to the invention.

DETAILED DESCRIPTION OF THE PREFERRED EMBODIMENTS

Figure 1A:
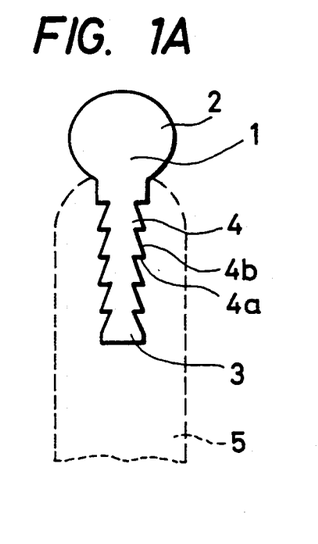
FIG. 1A is a complete view.
Figure 1B:
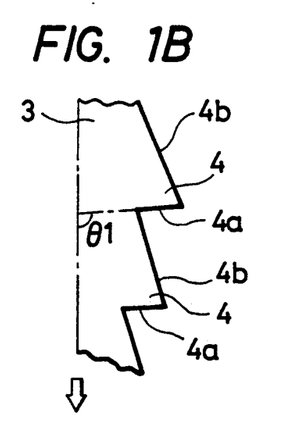
FIGS. 1B and 1C are partially expanded views.

Referring to FIGS. 1A to 1C, an embodiment of the present invention will be described. In FIG. 1A, one of the members 1 of an artificial joint engages with the other member (not shown) and the combination comprises a portion 2 forming a curve and an anchor portion 3. The anchor portion 3 is square bar-shaped on the whole and comprises triangular bosses 4A on its sides. The boss 4 has two faces 4a, 4b and, as shown in FIG. 1B, the face 4a oriented to the direction of insertion of the anchor portion 3 (shown by an arrow) into a bone 5 is set at an angle of $\theta 1$ to the direction of insertion. The angle $\theta 1$ must be smaller than 100° and particularly angles of between 45° and 90° are preferred for the promotion of bone fixation.

Figure 1C:
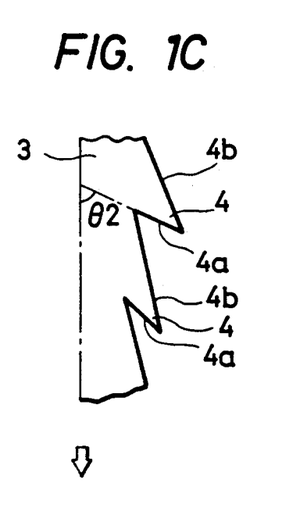

As a ligament acts to pull bones connected by a joint, the bone is pressed against the joint and, in that pressed state, the development of the bone tissue in that neighborhood is seen to increase to a greater extent, provided that the angle $\theta 1$ is smaller than 100°. For instance, the above-described phenomenon is also caused in the case of an acute angle of $\theta 2$ shown in FIG. 1C. Accordingly, the anchor portion of the artificial joint is quickly coupled and fixed to the bone 5.

Figure 2A:
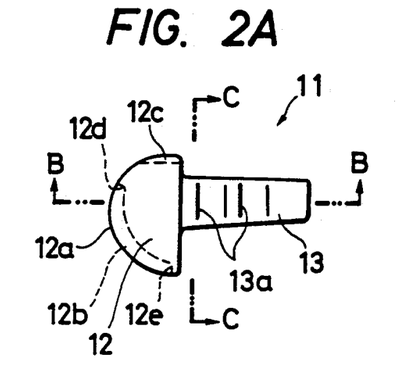
FIG. 2A is an elevated view, FIG. 2B, a top view.
Figure 2B:
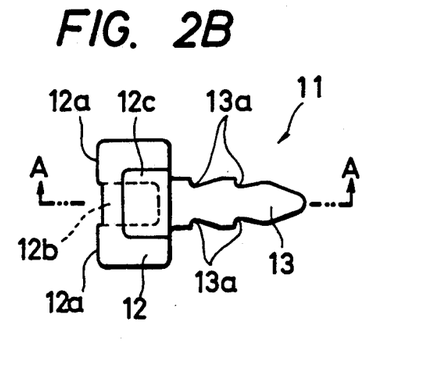
Figure 2C:
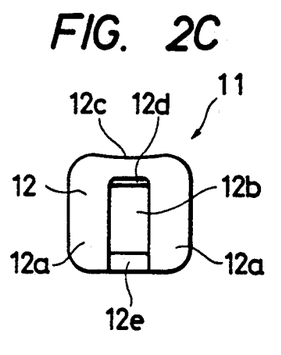
FIG. 2C, a left-hand side view.
Figure 2D:
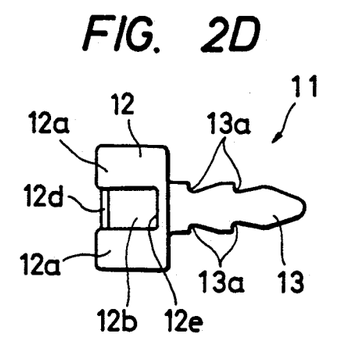
FIG. 2D, a bottom view.
Figure 2E:
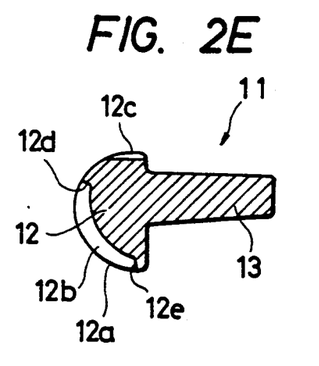
FIG. 2E, sectional view taken along line A—A of FIG. 2B.
Figure 2F:
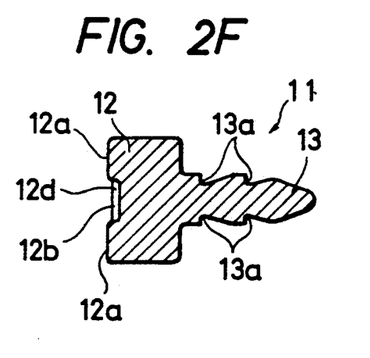
FIG. 2F, a sectional view taken on line B—B of FIG. 2A.
Figure 2G:
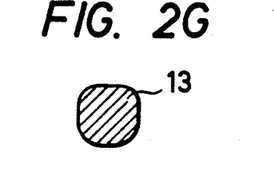
FIG. 2G, a sectional view taken on line C—C of FIG. 2A.
Figure 3A:
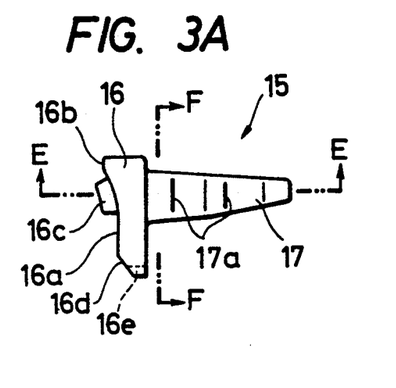
FIG. 3A is an elevational view.
Figure 3B:
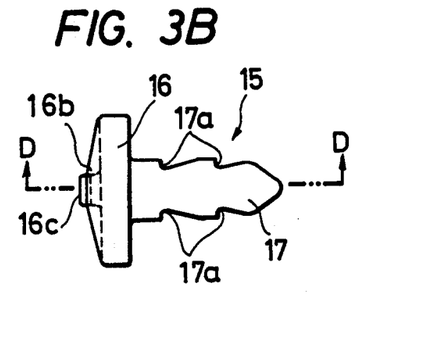
FIG. 3B, a top view.
Figure 3C:
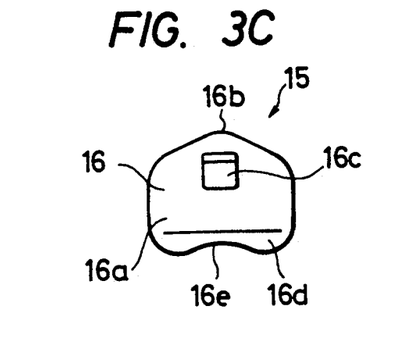
FIG. 3C, a left-hand side view.
Figure 3D:
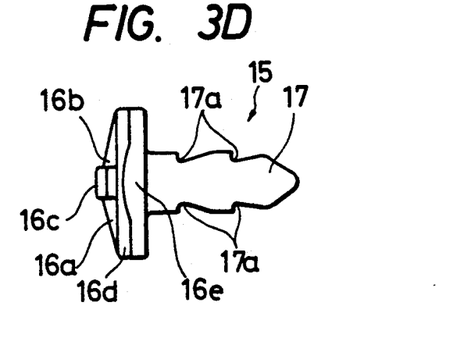
FIG. 3D, a bottom view.
Figure 3E:
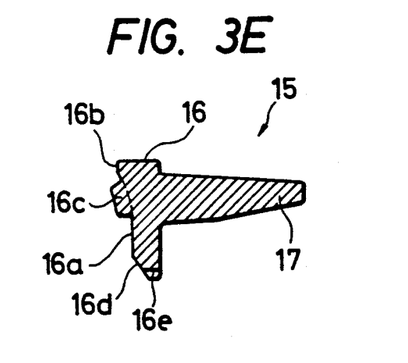
FIG. 3E, a sectional view taken on line D—D of FIG. 3B.
Figure 3F:
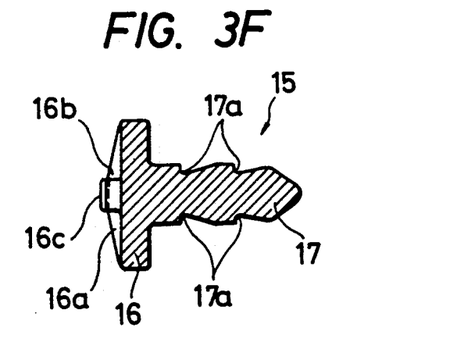
FIG. 3F, a sectional view taken on line E—E of FIG. 3A.
Figure 3G:
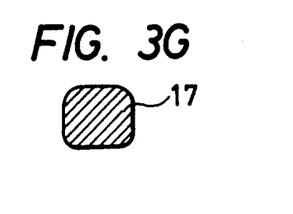
FIG. 3G, a sectional view taken on F—F of FIG. 3A.

Referring to FIGS. 2A and 2G, a first member comprises an anchor portion 13 and a slide portion 12 adapted to pivotally engage a slide portion of a second member described later. The slide portion 12 has a semi-cylindrical shape obtained by cutting a cylinder along the face including its axis. The anchor 13 is connected to a flat part of the slide portion 12. An arcuate groove 12b is cut in the center of a curved peripheral face 12a of the slide portion 12, opposite to the anchor 13. The arcuate groove 12b has a substantially rectangular shape in cross section. The groove 12b terminates at end walls 12d and 12e. A recess 12c for receiving the ligament is formed in the extending direction of the groove 12.

The anchor 13 is tapered, bar-shaped and square in cross section with rounded corners. Two grooves 13a are triangular in cross section and cut in the opposite faces of the anchor 13. Of the two cut faces of the grooves 13a, one on the side of the slide portion 12 is substantially perpendicular to the long axis of the anchor 13. The anchor 13 is inserted into a hole provided in the bone marrow and plays the role of fixing the artificial joint to the bone.

FIGS. 3A to 3G illustrates a second member on the finger tip side in the artificial joint of the present invention.

The second member 15 comprises an anchor portion 17 and a slide portion 16 adapted to pivotally engage the slide portion 12 of the first member. The slide portion 16 is substantially in the form of a pentagonal plate. A recessed face 16a opposite to the anchor 17 is curved toward an apex 16b, which protrudes from the face. A rectangular boss 16c curved following the curved face 16a is provided toward the apex 16b in the center of the curved face 16a. Moreover, the peripheral side opposite to the apex 16b is cut obliquely by a cut face 16d and the central portion of the periphery is provided with a gentle recess 16e for receiving a ligament.

The anchor 17 is disposed opposite to the curved face 16a the slide portion 16. The anchor 17 is tapered, bar-shaped and rectangular with rounded corners in cross-section. Two opposite sides of the anchor 17 are provided with two grooves 17a which are triangular in cross section. The shapes of the grooves 17a and the function of the anchor 17 are the same as those of the member 11.

The first and second members most suitably usable for finger joints should be 20-21 mm long in total. The joint portions 12 and 16 are preferably 5-8 mm long and 12-15 mm wide, and the anchors 13 and 17 are preferably 13-15 mm long and 4-5 mm wide.

Figure 4:
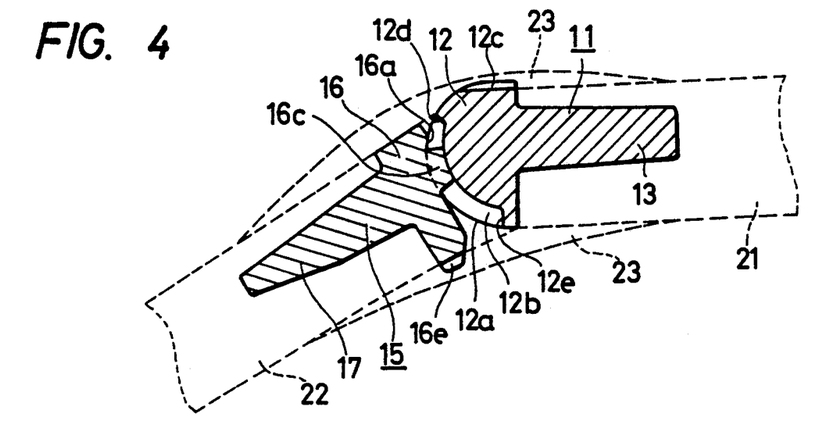
FIG. 4 is a sectional view illustrating the assembled artificial joint according to the present invention.

The first and second members 11 and 15 are combined together as shown in FIG. 4 and form a finger joint. FIG. 4 is a sectional view of the combination of the first and second members 11 and 15. The boss 16c of the second member 15 is inserted into the groove 12b of the first member 11 and slidably disposed therein. The peripheral face 12a, excluding part thereof, of the first member 11 substantially, slidably engages on the curved face 16a of the second member 15. The members 11 and 15 are movable by sliding the curved face 16a on the peripheral face 12a and simultaneously sliding the boss 16c in the groove 12b. The angle formed by the anchors 13 and 17 can thus be adjusted. The angle between the anchors 13 and 15 is changeable until the boss 16c contacts either of the end walls 12d, 12e of the groove 12b.

Figure 5:
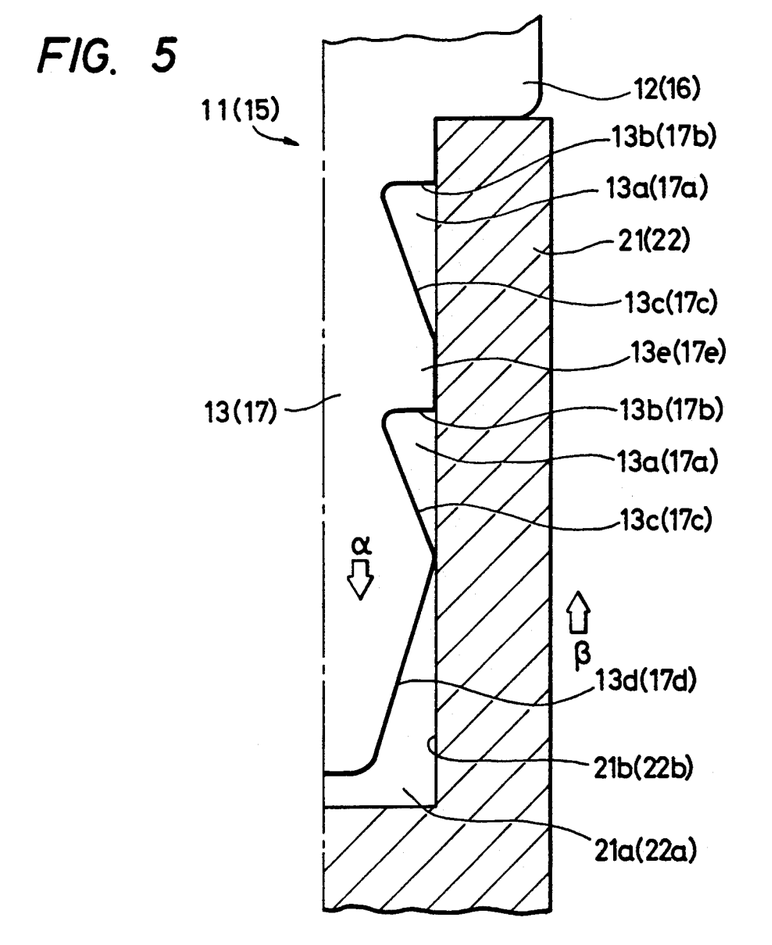
FIG. 5 is the enlarged portion of the same.

As shown in a blown-up sectional view of FIG. 5, each of the members 11 and 15 is arranged in such a manner that it contacts the inner wall 21b (22b) of a hole 21a (22a) provided in the bone 21 (22). Force is applied to the member 13 in the direction of insertion, i.e., the direction shown by an arrow $a$ by the ligament 23 coupling the bones 21, 22. Force is applied to the bone 21 (22) in the direction shown by an arrow $\oplus$. One face 13b (17b) of the inner faces 13b (17b) and 13c (17c) of the groove 13a (17a) is arranged at an angle of about 90° to the direction of insertion of the anchor 13 (17). When the anchor is thus disposed, bone tissue grows more quickly from the inner wall face 21b (22b) of the hole 21a (22a) of the bone 21 (22) over the surface 13b (17b) than over the other faces 13c (17c), 13d (17d). Consequently, the groove 13a (17a) is quickly filled with the bone tissue and the connection of the anchor 13 (17) with the bone 21 (22) is smoothly implemented.

According to this embodiment, the surface of the groove 13a (17a) is defined by the faces 13b (17b) and 13c (17c). The faces 13c (17c). and 13b (17b) are also used to form the boss 13e (17e). A boss is thus formed on the surface of the anchor 13 (17). The face away from the direction of the insertion may form an angle of 100° to the direction of insertion.

Although the groove 13a (17a) or the boss 13e (17e) is provided on only two opposite sides of the anchor according to this embodiment, it may be provided on all four sides.

As set forth above, the embodiment of the artificial joint allows itself to be joined to the bone quickly because of the presence of the face 13b (17b) provided in the direction of insertion of the anchor 13 (17).

Moreover, because the artificial joint according to the embodiment is simple in construction, it is readily manufactured and satisfies requirements for the finger joint in that it is smoothly pivotable in two directions by a desired angle. As the joint is made to contact two faces 12a, 16a it offers high strength and durability, whereas it can simply be assembled during an operation by inserting the knobs 13, 17 into bone marrow holes and the boss 6c into the groove 2b.

Figure 6A:
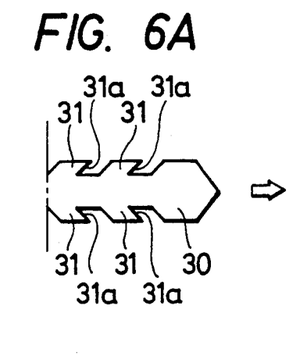
FIG. 6A is an elevated view of another anchor and FIG. 6B is a top view of the same.
Figure 6B:
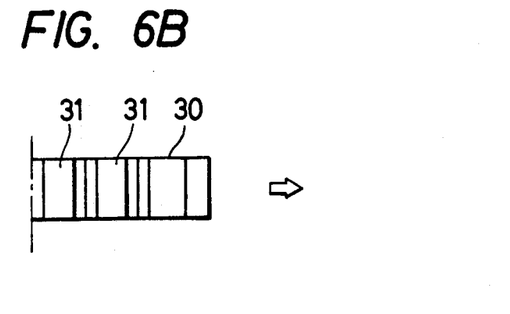
Figure 7A:
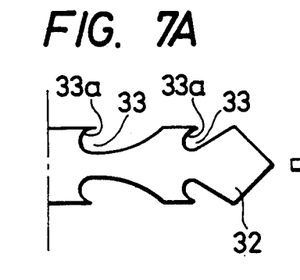
FIG. 7A is an elevational view of still another anchor portion and FIG. 7B is a top view of the same.
Figure 7B:
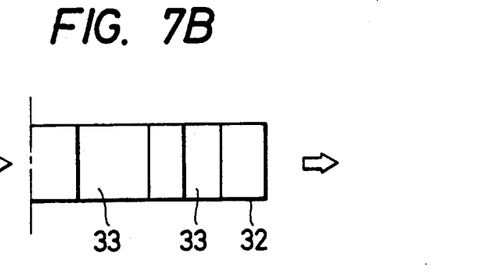
Figure 8A:
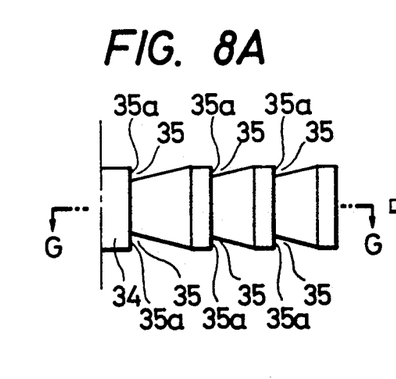
FIG. 8A is an elevated view of a further anchor portion and FIG. 8B is a sectional view taken on line G—G of FIG. 8A.
Figure 8B:
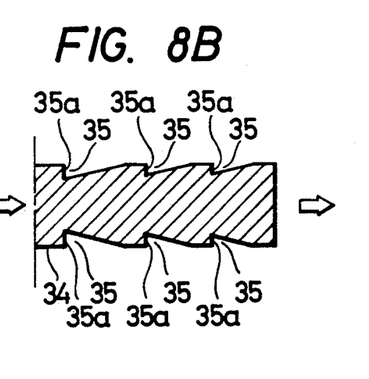

Anchor structures other than that of the above-described embodiment, such as those shown in FIGS. 6 to 8 may be used.

A square bar-shaped anchor 30 shown in FIGS. 6A and 6B is equipped with a boss 31 having the shape of a parallelogram in cross section. FIG. 6A illustrates an elevational view of the anchor and FIG. 6B a top view of the same. The anchor 30 has the boss 31 with a side face 31a oriented in the direction of insertion (shown by an arrow). The side face is used to promote its connection with the bone. An angle to the direction of insertion is set smaller than 90°.

A square bar-shaped anchor 32 shown in FIGS. 7A and 7B is provided with a groove 33 which is semielliptical in cross section. FIG. 7A illustrates an elevational view of the anchor and FIG. 7B a top view of the same. Part 33a of the inner face of a groove 33 in the direction of insertion (shown by an arrow) of the anchor 32 is used to promote the connection with the bone. Although the face is curved in this case, the inclination of the face of that part at smaller than 100° to the direction of insertion is acceptable.

A rod-shaped anchor is shown in FIGS. 8A and 8B, which is supplied with a circumferential groove 35, triangular in cross section, over its whole periphery. One face 35a of the inner face of the circumferential groove 35 in the direction of insertion (shown by an arrow) of the knob is used to promote the connection with the bone. In that case, the face 35a is roughly perpendicular to the anchor 34.

Although reference has not been made to the quality of material for use in the artificial joint according to the present invention, ceramics should preferably be used because they are free from virulence and allow the quick development of bone tissues on the surface and readily combine with the bone. Of ceramics, sintered $ZrO_2$ is particularly preferred in terms of mechanical strength and tenacity. However, as a ceramic surface is sufficient, metal can be used to form the body and the surface may be coated with ceramics to improve strength and durability.

In the structure of the anchor of the artificial joint according to the present invention, a recess or boss is provided on the surface of the anchor and the face forming the recess or boss which faces the direction of insertion of the anchor is set at an angle of smaller than 100° to that direction. The growth of the bone tissue is accordingly promoted and the anchor is allowed to combine with the bone quickly and be fixed to the bone.

Still another embodiment of the invention relates to an artificial fixed knuckle bone suitable for use as a bone substitute employed to fix a finger joint that has ceased to function because of diseases such as rheumatism and bone ulcers. A doglegged or circular bone prosthesis has been prepared from ceramics. Such a bone prothesis, for replacing a living bone, is inserted and fixed at a finger joint. In the conventional structure, new bone hardly forms around the bone prothesis, which is thus inferior in adhesion and stability to the living body.

Figure 10A:
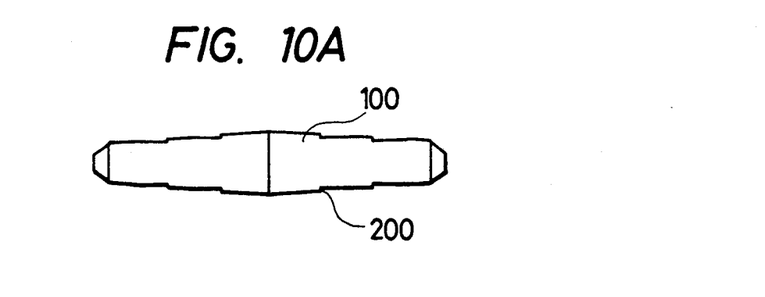
FIGS. 10A and 10B are a plan view and a side elevational view of an artificial fixed finger bone according to the invention.
Figure 10B:
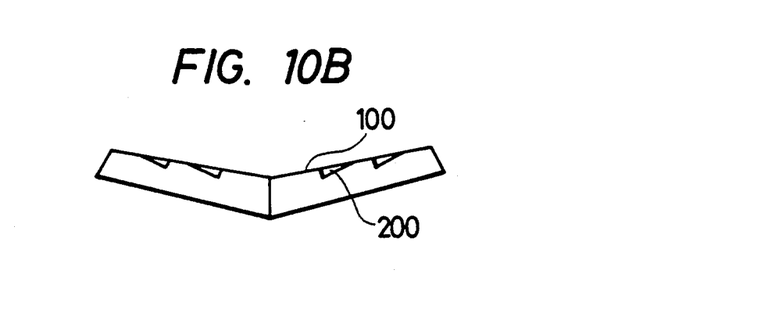

The embodiment of the present invention is intended to solve the above problems and to provide an artificial fixed knuckle bone superior in adhesion and stability to a diseased bone. FIGS. 10A and 10B are elevational and top view, respectively, of an artificial fixed knuckle bone according to the invention. An artificial fixed knuckle bone 100 which is doglegged in vertical cross section is shown. The bone 100 comprises a ceramic surface and a plurality of sectionally sawtooth-like recesses 200 provided on both faces of the artificial fixed knuckle bone as seen in FIG. 10B. The recesses 200 must be cut in the reverse direction to the left and right sides as seen in FIG. 10B with the bent portion as a boundary roughly at the center in the longitudinal direction of the artificial fixed knuckle bone 100.

When the artificial fixed knuckle bone 100 according to the present invention is inserted in the finger joint of a living body, compression stress is applied from both sides of the finger tip and the base of the finger with the bent portion as a boundary roughly at the center. However, the presence of the recesses 200 in the reverse direction with the bent portion as a boundary act to resist the compression stress from either side and hold the bone stably therein. There is initially a wedge-shaped space between the recesses 200 and the surrounding bone when the artificial fixed knuckle bone 100 is inserted. As time elapses, new bone is formed, causing the artificial fixed knuckle bone 100 to join to the living body. The stable catching or adhesive functions are substantial when an angle between the face in the catching cuts 200 resisting the compression stress and the direction of the compression stress is 90 degrees in the wedge-shaped space. As long as the surface of the artificial fixed knuckle bone according to the present invention is ceramic, it is harmless to the living body. Needless to say, it is acceptable to prepare the whole body from ceramics, coat the surface of a metal body with ceramics or provide a ceramic film on the surface of a metal body. However, a sintered body of zirconia, composite sintered body of zirconia and alumina or high strength sintered body of calcium phosphate disclosed in Japanese Pat. Appln. Laid-Open No. 55-140756 is preferable in terms of tenacity, mechanical strength and adhesion to a living body.

Figure 11A:
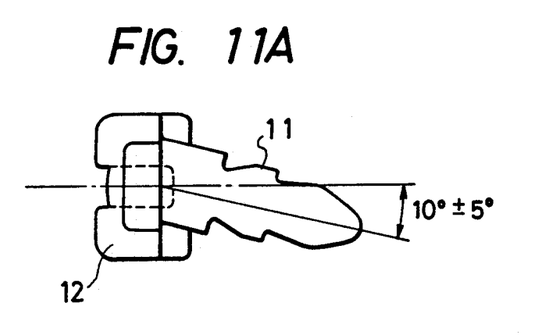
FIGS. 11A, 11B, and 11C an embodiment of the present invention particularly suited for replacing the joint of a human little finger.
Figure 11B:
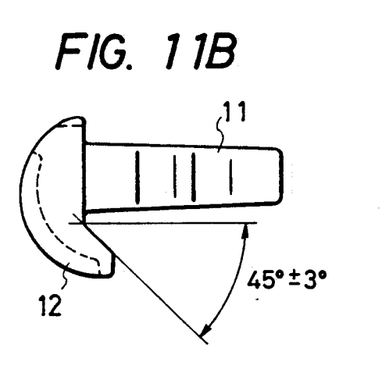
Figure 11C:
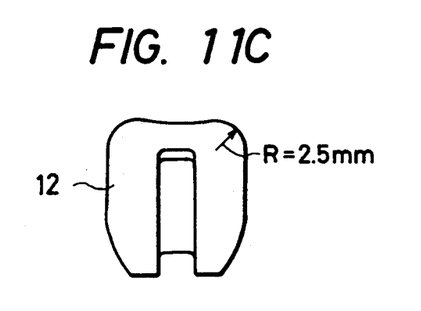

Yet another embodiment of the present invention is shown in FIGS. 11a, 11b and 11c. This embodiment is directed to applications of the ceramic bone joint particularly to a human forefinger and a human little finger. In order to apply the invention to a human forefinger or little finger, it is preferable that the anchor 11 be bent slightly with respect to the slide portion 12 as shown in FIG. 11a. It is also preferable that the slant angle be in a range from about 5° to about 15°. Also the portion A of the slide portion in FIG. 11b has a slant surface defined by an angle of 45° ±3°. This structure allows the bone marrow to be cut to be reduced. In order to simulate the human joint structure, it is preferable to round the corner of the sliding bone joint to an extent defined by a radius of curvature of 2.5 mm as shown in FIG. 11c.

Working Examples $ZrO_2$ powder of 96 mol% and $Y_2O_3$ of 4 mol% having an average grain size of 0.1 m were mixed, molded by a rubber press and heated at a temperature of 1,550° C. for one hour as holding time to obtain an artificial fixed knuckle bone 100 comprising 80% of tetragonal zirconia and 20% of cubic zirconia having a doglegged shape. A sample for measuring the strength was separately prepared under the same conditions as those for the artificial fixed knuckle bone 100 except that the latter is cubic in shape. The bend resistant strength measured was 130 Kg/mm². When the artificial fixed knuckle bone 100 was inserted into the living body, it was stably joined because of compression stress applied from both sides of the tip and the base of the finger and, as time elapsed, new bone was formed in the recess of the recesses 200. Excellent harmless adhesion to the living body was thus provided.

As set forth above, the artificial fixed knuckle bone according to the invention is joined at the finger joint of the living body stably and harmlessly.

Having described the invention with respect to the preferred embodiments shown in the accompanying drawing, it is further understood by those skilled in the art that various changes and modifications may be made in the invention without departing from the spirit and scope thereof.

What is claimed is:

1. An artificial bone joint for joining first and second bones comprising:
    a first member including a first elongated anchor portion having a proximal end, a distal end, and a first central longitudinal axis extending from said proximal end to said distal end in a first direction, and including a first sliding portion having a convex curved surface;
    a second member including a second elongated anchor portion having a proximal end, a distal end, and a second central longitudinal axis extending from said proximal end to said distal end in a second direction, and including a second sliding portion having a concave curved surface for pivotally engaging said convex surface;
    said first anchor portion including a plurality of axially spaced first recesses forming at least one pair of first anchor bosses symmetrically opposed to each other about said first central longitudinal axis having perimetrical surfaces defining a maximum cross-sectional area of the first anchor portion and each of said first recesses having a proximal end wall defined by a radially extending surface transverse to the longitudinal axis and a bottom surface inclined from a proximal to distal direction at a first angle of less than 90° with the proximal end wall to form a catching structure for said first member; and
    said second anchor portion including a plurality of axially spaced second recesses forming at least one pair of second anchor bosses symmetrically opposed to each other about said second central axis having perimetrical surfaces defining a maximum cross-sectional area of the second anchor portion and each of said second recesses having a proximal end wall defined by a radially extending surface transverse to the longitudinal axis and a bottom surface inclined from a proximal to distal direction at a first angle of less than 90° with the proximal end wall to form a catching structure for said second member.

2. An artificial bone joint according to claim 1, wherein each sad recess is semielliptical in cross section.

3. An artificial bone joint for joining first and second bones comprising:
    a first member including a first elongated anchor portion having a proximal end, a distal end, and a first central longitudinal axis extending from said proximal end to said distal end in a first direction, and including a first sliding portion having a convex curved surface;
    a second member including a second elongated anchor portion having a proximal end, a distal end, and a second central longitudinal axis extending from said proximal end to said distal end in a second direction, and including a second sliding portion having a convex curved surface for pivotally engaging said convex surface;
    said first anchor portion including a plurality of axially spaced first recessed forming at least one pair of first anchor bosses symmetrically opposed to each other about said first central longitudinal axis having perimetrical surfaces defining a maximum cross-sectional area of the first anchor portion and each of said first recessed having a proximal end wall defined by a radially extending surface transverse to the longitudinal axis and a bottom surface inclined from a proximal to distal direction at a first angle of less than 90° with the proximal end wall to form a catching structure for said first member; and
    said second anchor portion including a plurality of axially spaced second recessed forming at least one pair of second anchor bosses symmetrically opposed to each other about said second central axis having perimetrical surfaces defining a maximum cross-sectional area of the second anchor portion and each of said second recesses having a proximal end wall defined by a radially extending surface transverse to the longitudinal axis and a bottom surface inclined from a proximal to distal direction at a first angle of less than 90° with the proximal end wall to form a catching structure for said second member;
    wherein each said anchor boss has a shape of a parallelogram in cross section.

4. An artificial bone joint according to claim 1, wherein said first and second anchor portions each have substantially square cross-sections.

5. An artificial bone joint according to claim 1, wherein said first and second angles are between about 45° and about 90°.

6. An artificial bone joint according to claim 4, wherein said first and second angles are between about 45° and about 90°.

7. An artificial fixed bone joint for joining first and second bones comprising:
    an elongated substantially V-shaped member having a first elongated anchor portion having first and third ends opposite to each other and a first central longitudinal axis extending from said third end to said first end; and
    a second elongated anchor portion having second and fourth ends opposite to each other and a second central longitudinal axis extending from said fourth end to said second end, said second portion being attached at said fourth end to said third end of said first portion, said first and second axis forming a fixed angle of less than 180 degrees;
    said first anchor portion having first and third surfaces diametrically opposite to each other, said first and third surfaces extending from said first end to said third end, said second anchor portion having second and fourth surfaces diametrically opposite to each other, said second and fourth surfaces extending from said second end to said fourth end, said first and second surfaces being substantially continuouslly even, said third and fourth surfaces facing each other;
    at least one first substantially wedge-shaped recess formed in the third surface, each first recess forming a first boss having a boss surface facing said first end and defining one end of said first recess, said first boss surface forming an angle of less than 100 degrees with the first axis to form a catching structure for said third surface; and at least one second substantially wedge-shaped recess formed in the fourth surface, each second recess forming a second boss having a boss surface facing said second end and defining one end of said second recess, said second boss surface forming an angle of less than 100 degrees with the second axis to form a catching structure for said fourth surface.

8. The artificial bone joint according to claim 7, wherein said first and second members comprise approximately 80% tetragonal zirconia and approximately 20% cubic zirconia and have a bend resistant strength of 130 Kg/mm².

9. An artificial bone joint for joining first and second bones comprising:

a first member including a first anchor portion having a proximal end, a distal end, and a first central longitudinal axis extending from said proximal end to said distal end in a first direction, and including a first sliding portion having a convex curved surface having a substantially semicylindrical shape and a plane side surface abutting said proximal end of said first anchor portion and having a groove formed in the convex curved surface; and a second member including a second anchor portion and including a second sliding portion having a concave curved surface substantially in a form of a pentagon and having a boss formed on the concave curved surface, wherein the concave curved surface is in sliding contact with said convex curved surface;

wherein said first central longitudinal axis forms ann angle in a range from about 5 degrees to about 15 degrees with the direction perpendicular to the plane side surface.

10. An artificial bone joint according to claim 1, wherein said convex curved surface has a substantially semicylindrical shape and a plane side surface abutting said proximal end of said first anchor portion and wherein said first direction forms an angle in a range from about 5 degrees to about 15 degrees with a direction perpendicular to the plane side surface.

11. An artificial bone joint according to claim 10, wherein each of said first recess and said second recess forms a second concave surface.

12. An artificial bone joint for joining first and second bones comprising:

a first member including a first elongated anchor portion having a proximal end, a distal end, and a first central longitudinal axis extending from said proximal end to said distal end in a first direction, and including a first sliding portion, said first sliding portion having a convex curved surface substantially of a semicylindrical shape, a groove formed in the convex curved surface, and a first plane surface extending perpendicularly to the first direction, said first plane surface being for abutment contact with an end surface of the first bone;

a second member including a second elongated anchor portion having a proximal end, a distal end, and a first central longitudinal axis extending from said proximal end to said distal end in a second direction, and including a second sliding portion, said second sliding portion having a first concave surface substantially in a form of a pentagon, a limiting boss formed on the first concave surface, and a second plane surface extending perpendicularly to the second direction, said second plane surface being for abutment contact with an end surface of the second bone, the first concave surface being in sliding contact with and pivotally engaging said convex curved surface; and limiting means inserted into said groove for limiting an angle of flexion and extension of the joint;

wherein said joint further includes a first anchor portion on said first member and including at least one first axially extending recess forming a first anchor boss having a first axially extending perimetrical surface defining a maximum cross-sectional area of said first anchor portion and a first radially extending surface facing said first direction at one end of said first recess, said first radially extending surface forming an angle of less than 100° with the first direction to form a first catching structure for said first member; and a second anchor portion on said second member and including at least one second axially extending recess forming a second anchor boss having a second axially extending perimetrical surface defining a maximum cross-sectional area of said second anchor portion and a second radially extending surface facing said second direction at one end of said second recess, said second radially extending surface forming an angle of less than 100 ° with the second direction to form a second catching structure for said second member.

13. An artificial bone joint according to claim 12, wherein said first sliding portion has two vertical surfaces space from said second member wherein said two vertical surfaces lie in different planes and are joined by a slant surface formed at an angle of approximately 45° from horizontal.

14. An artificial bone joint according to claim 10 wherein said first member has at least one rounded corner having a radius of curvature of approximately 2.5 mm.

15. An artificial bone joint according to claim 10, wherein said convex curved surface has a center and wherein said groove is an arcuate groove cut in the center of said convex curved surface, having a substantially a rectangular shape in cross section, and terminating at end walls positioned at each longitudinal end of the arcuate groove.

16. An artificial bone joint according to claim 12, wherein said limiting boss is positioned toward an apex of said first concave surface, has a substantially rectangular shape, and has a second concave surface which is spaced from said first concave surface and which is substantially parallel to said first concave surface.

17. An artificial bone joint of claim 1, wherein the convex curved surface is substantially of a semicylindrical shape and the concave curved surface is in a form of a pentagon.

18. An artificial bone joint of claim 17, further comprising means for limiting an angle of flexion and extension of the joint, said angle limiting means including a groove formed in the convex curved surface and a limiting boss formed on the concave curved surface, wherein the concave curved surface is in sliding contact with the convex curved surface.

19. The artificial bone joint of claim 18, wherein the first sliding portion further comprises a first plane surface extending perpendicularly to the first direction, said first plane surface being for abutment contact with an end surface of the first bone, and wherein the second sliding portion further comprises a second plane surface extending perpendicularly to the second direction, said second plane surface being for abutment contact with an end surface of the second home.

20. An artificial bone joint according to claim 17, wherein said first sliding portion has two vertical surfaces spaced from said second member wherein said two vertical surfaces lie in different planes and are joined by a slant surface formed at an angle of approximately 45 degrees from horizontal.

21. An artificial bone joint according to claim 17, wherein said first sliding portion has at least one rounded corner having an arcuate surface having a radius of approximately 2.5 mm.

22. An artificial bone joint according to claim 17, including a groove formed in said convex curved surface, wherein said convex curved surface has a center and wherein said groove is an arcuate groove cut in thee center of said convex curved surface, having a substantially rectangular shape in cross section, and terminating at end walls positioned at each longitudinal end of the arcuate groove.

23. An artificial bone joint according to claim 17, including a limiting boss formed on said concave curved surface, wherein said limiting boss is positioned toward ann apex of aid concave curved surface, has a substantially rectangular shape, and has a second concave surface which his spaced from said concave curved surface and which is substantially parallel to said concave curved surface.

* * * * *